US007943820B2

(12) United States Patent
Tasaka et al.

(10) Patent No.: US 7,943,820 B2
(45) Date of Patent: *May 17, 2011

(54) GENETICALLY MODIFIED PLANTS PRODUCING LACTOSYLCERAMIDE AND UTILIZATION THEREOF

(75) Inventors: Yasushi Tasaka, Sapporo (JP); Takeshi Matsumura, Sapporo (JP); Kouki Matsuo, Sapporo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 882 days.

This patent is subject to a terminal disclaimer.

(21) Appl. No.: 11/574,466

(22) PCT Filed: Aug. 31, 2005

(86) PCT No.: PCT/JP2005/015899
§ 371 (c)(1),
(2), (4) Date: Sep. 17, 2007

(87) PCT Pub. No.: WO2006/025443
PCT Pub. Date: Mar. 9, 2006

(65) Prior Publication Data
US 2008/0115242 A1    May 15, 2008

(30) Foreign Application Priority Data
Aug. 31, 2004  (JP) ................................ 2004-253287

(51) Int. Cl.
*C12N 15/82* (2006.01)
*A01H 5/00* (2006.01)

(52) U.S. Cl. ........ 800/288; 800/278; 800/295; 800/298; 435/419; 435/468

(58) Field of Classification Search ........................ None
See application file for complete search history.

(56) References Cited

U.S. PATENT DOCUMENTS
5,294,593 A * 3/1994 Khan ............................ 504/100
7,619,136 B2 * 11/2009 Tasaka et al. .................. 800/288

FOREIGN PATENT DOCUMENTS
| JP | 10-503474 A | 3/1998 |
| JP | 10-295371 A | 11/1998 |
| JP | 2003-535965 A | 12/2003 |
| WO | WO 95/28376 A1 | 10/1995 |
| WO | WO 01/97819 A1 | 12/2001 |

OTHER PUBLICATIONS

Palacpac et al. Stable expression of human B1,4-galactosyltransferase in plant cells modifies N-linked glycosylation patterns. (1999) PNAS; vol. 96; pp. 4692-4697.*
Tanaka et al. Ozone tolerance and glutathione reductase in tobacco cultivars. (1990) Agric. Biol. Chem.; vol. 54; pp. 1061-1062.*
Bakker et al. Galactose-extended glycans of antibodies produced by transgenic plants. (2001) PNAS; vol. 98; pp. 2899-2904.*
Nomura et al. Purification, cDNA cloning, and expression of UDP-Gal:glucosylceramide beta-1,4-galactosyltransferase from rat brain. (1998) JBC; vol. 273; pp. 12570-13577.*
Sato et al. MOlecular cloning of a human cDNA encoding beta-1,4-galactosyltransferase with 37% identity to mammalian UDP-Gal:GlcNAc beta-1,4-galactosyltransferase. (1998) PNAS; vol. 95; pp. 472-477.*
Rosin, L. J. Transgenic plants bio-farming for the future. (2004) Chapter Five in "Bioprocess International"; publisher: BioProcess International, Westborough, MA pp. 52-61.*
Datta et al.; Bioengineered 'Golden' Indica Rice Cultivars With β-carotene Metabolism in the Endosperm With Hygromycin and Mannose Selection Systems; Plant Biotechnology Journal; 2003; 1; pp. 81-90.
Francois et al.; The Determination of Mannose in Hen's-Egg Albumin by Radioisotope Dilution; Blochem. Journal; 1962; 83; pp. 335-341.
Harwood, J.L.; What's So Special About Plant Lipids? Plant Lipid Biosynthesis; Nov. 1998; 67; pp. 1-26.
Hasegawa et al.; Synthesis of Cerebroside, Lactosyl Ceramide, and Ganglioside GM3, Analogs Containing β-Thioglycosidically Linked Ceramide; Carbohydrate Research; 1991; 214; pp. 43-53.
Imai et al.; Structure and Distribution of Cerebroside Containing Unsaturated Hydroxy Fatty Acids in Plant Leaves; Biosci. Biotech. Biochem.; 1995; 59; pp. 1309-1313.
Karlsson, Karl-Anders; Animal Glycosphingolipids as Membrane Attachment Sites for Bacteria; Annu. Rev. Biochem.; 1989; 58; pp. 309-350.
Kelly et al.; Green Light for Galactolipid Trafficking; Current Opinion in Plant Biology; 2004; 7; pp. 262-269.
Miege et al.; Biochemical and Topological Properties of Type A MGDG Synthase, a Spinach Chloroplast Envelope Enzyme Catalyzing the Synthesis of Both Prokaryotic and Eukaryotic MGDG; Eur. J. Biochem.; 1999; 265; pp. 990-1001.
Ohnishi et al.; Characterization of Sphingolipids in Spinach Leaves; Biochimica et Biophysica Acta; 1983; 752; pp. 416-422.
Palacpac et al.; Stable Expression of Human Beta 1,4-galactosyltransferase in Plant Cells Modifies N-Linked Glycosylation Patterns; Proceedings of the National Academy of Sciences of the United States of America; 1999; 96; pp. 4692-4697.
Sanders et al.; Comparison of Cauliflower Mosaic Virus 35S and Nopaline Synthase Promoters in Transgenic Plants; Nucleic Acids Research; 1987; vol. 15; pp. 1543-1558.
Trinchera et al.; Localization in the Golgi Apparatus of Rat Liver UDP-Gal: Glucosylceramide B1-4Galactosyltranserase; Biochemistry; 1991; vol. 30; pp. 2719-2724.
Amado et al.; Identification and Characterization of Large Galactosyltransferase Gene Families: Galactosyltransferase For All Functions; Biochimica et Biophysica Acta 1473 (1999) pp. 35-53.

(Continued)

*Primary Examiner* — Cathy Kingdon Worley
(74) *Attorney, Agent, or Firm* — Foley & Lardner LLP; James F. Ewing; Michel Morency

(57) ABSTRACT

Plant expression vectors comprising an ORF of an isoform gene (β1,4GT5) of human β1,4-galactosyltransferase were constructed. Then, the vectors were introduced into tobacco using plant gene-recombination techniques, and transformed tobacco was made. Analysis of the obtained transformed tobacco showed that more than 200 μg of lactosylceramide was produced from 1 g of fresh leaves. Accordingly, the present invention made it possible to mass synthesize lactosylceramide by using recombinant plants.

7 Claims, 7 Drawing Sheets

OTHER PUBLICATIONS

Bligh et al.; A Rapid Method of Total Lipid Extraction and Purification; Canadian Journal of Biochemistry and Physiology; Aug. 1959; vol. 37, No. 8; pp. 911-917.

Cohen et al.; Roles of Globotriosyl—and Galabiosylceramide in Verotoxin Binding and High Affinity Interferon Receptor; The Journal of Biological Chemistry; vol. 262, No. 35; 1987; pp. 17088-17091.

Furukawa et al.; B-1,4-Galactosylation of N-Glycans is a Complex Process; Biochimica et Biophysica Acta 1473; 1999; pp. 54-66.

Kelly et al; Disruption of the Two Digalactosyldiacylglycerol Synthase Genes *DGD1* and *DGD2* in Arabidopsis Reveals the Existence of an Additional Enzyme of Galactolipid Synthesis; The Plant Cell; Nov. 2003; vol. 15; pp. 2694-2706.

Lindberg et al.; Identification of the Carbohydrate Receptor for Shiga Toxin Produced by *Shigella dysenteriae* Type 1; The Journal of Biological Chemistry; Feb. 1987; vol. 262, pp. 1779-1785.

Lynch, Daniel V.; Sphingolipids; Lipid Metabolism in Plants; 1993; pp. 285-308.

Sato et al.; Molecular Cloning of a Human cDNA Encoding β-1,4-galactosyltransferase with 37% Identity to Mammalian UDP-Gal: GlcNAc β-1, 4-galactosyltransferase; Proceedings of the National Academy of Sciences of the United States of America; 1998; vol. 95; pp. 472-477.

Sayanova et al.; Expression of a Borage Desaturase cDNA Containing an N-terminal Cytochrome b5 Domain Results in the Accumulation of High Levels of Delta 6-desaturated Fatty Acids in Transgenic Tobacco; Proceedings of the National Academy of Sciences of the United States of America; Apr. 1997; vol. 94; pp. 4211-4216.

Shimojima et al.; Cloning of the Gene for Monogalactosyldiacylglycerol Synthase and its Evolutionary Origin; Proceedings of the National Academy of Sciences of the United States of America; Jan. 1997; vol. 94; pp. 333-337.

Stromberg et al.; Idenification of Carbohydrate Structures that are Possible Receptors for Neisseria Gonorrhoeae; Proceedings of the National Academy of Sciences of the United States of America; Jul. 1988; vol. 85; pp. 4902-4906.

Stromberg et al.; Studies on the Binding of Bacteria to Glycolipids; Federation of European Biochemical Societies; 1988; vol. 232; pp. 193-198.

Tozawa et al.; Characterization of Rice Anthranilate Synthase α-Subunit Genes OASA1 and OASA2. Tryptophan Accumulation in Transgenic Rice Expressing a Feedback-Insensitive Mutant of OASA1; Plant Physiology; Aug. 2001; vol. 126; pp, 1493-1506

Wood et al.; Localization in the Golgi Apparatus of Rat Liver UDP-Gal: Glucosylceramide B1-4Galactosyltransferase; Biochemistry; 1991; vol. 30; pp. 2719-2724.

Voelker et al.; Fatty Acid Biosynthesis Redirected to Medium Chains in Transgenic Oilseed Plants; Science; Jul. 1992; vol. 257; pp. 72-74.

Watarai et al.; Inhibition of Vero Cell Cytotoxic Activity in *Escherichia coli* O157:H7 Lysates by Globotriaosylceramide, Gb3, from Bovine Milk; Biosci. Biotechnol. Biochem.; Feb. 2001; vol. 65; pp. 414-419.

Ye et al.; Engineering the Provitamin A (β-Carotene) Biosynthetic Pathway into (Carotenoid-Free) Rice Endosperm; Science; Jan. 2000; vol. 287; pp. 303-305.

International Search Report; PCT/JP2005/015899; Date of Mailing Nov. 15, 2005, 2 pages.

Hennet, T., "The Galactosyltransferase Family," CMLS, Cell. Mol. Life Sci. 59 (2002), pp. 1081-1095.

Ito, Makoto, "Glycosphingolipids: Structure, Localization and Metabolism," http:/www.glycoforum.gr.jp/science/word/glycolipid/GLA00E.html, pp. 1-3, originally published Jun. 15, 1998.

Pomorski, et al., "Lipid Flippases and Their Biological Functions," Cell. Mol. Life Sci. 63 (2006), pp. 2908-2921.

Yasushi Tasaka; Kumikae Shokubutsu o Mochiita Dobutsugata Toshishitsu no Seisan;01D Heisei 14 Nen, Kagaku Gijutsu Shinko Choseihi Shiken Kenkyu Jicchi Keikaku Keizoku Kadai, Oct. 2002, p. 93. (English translation).

* cited by examiner

GENETICALLY MODIFIED PLANTS PRODUCING LACTOSYLCERAMIDE AND UTILIZATION THEREOF

RELATED APPLICATIONS

The present application claims priority as a national stage application of International Patent Application serial number PCT/JP2005/015899 filed on Aug. 31, 2005, which claims the benefit of priority to Japanese Application No. 2004-253287, filed Aug. 31, 2004, the contents of which are hereby incorporated by reference in their entireties.

TECHNICAL FIELD

The present invention relates to genetically modified plants producing lactosylceramide, a major starting substance for the biosynthesis of animal-type sphingoglycolipids, and to the production of animal-type sphingoglycolipids by using the plants.

BACKGROUND ART

Animal-type sphingoglycolipids are utilized as chemical products in raw materials of medicines and cosmetics. Sugar chains serve as receptors for various viruses including influenza virus and bacterial toxins (Non-Patent Document 1), and are therefore prospective as a novel remedy for these infectious diseases in early-stage practical application, which does not depend on antibiotics and chemically synthesized medical materials (Patent Documents 1 and 2). For example, it is known that ceramide trihexoside is a receptor for Vero toxin (toxin produced by *Escherichia coli* O-157) and Shiga toxin (toxin produce by dysentery bacilli) to bind to cell surface (Non-Patent Documents 2 and 3), and that lactosylceramide is a receptor for gonococci and Propionibacterium (bacteria causing dermatitis) to infect cells (Non-Patent Documents 4 and 5). However, conventional production methods which collect materials from animal brain have a problem of infectious diseases such as BSE (bovine spongiform encephalopathy), and artificial synthesis has the drawback of being difficult and costly.

Examples of research on the production of useful substances by using genetically modified plants have been recently reported (Non-Patent Documents 6 to 10). The merits of those methods are low cost, absence of carbon dioxide release and no risk of contamination by animal infectious diseases.

The fundamental structure of almost all species of sphingoglycolipids is lactosylceramide, and the variety of sphingoglycolipids, which is said to have more than 300 species, are biosynthesized in animal tissues by adding sugar chains to lactosylceramide. It is known that lactosylceramide can be synthesized from its precursor, glucosylceramide, by a sugar transfer reaction with β1,4-galactosyltransferase (β1,4GT) (Patent Document 3). Although plants have glucosylceramide, they cannot produce lactosylceramide due to the lack of β1,4GT, and as a result, they cannot produce animal-type glycolipids.

A research example reported the transfer of galactose to proteins by introducing hβ-1,4-GalT1 (Accession Number: X55415 or X13223), which is an isozyme of β1,4GT, into tobacco cells (not a plant body) cultured in a liquid medium (Non-Patent Document 11), but no example reports the transfer of sugars to lipids.

Technical literatures relating to the invention of the present application are shown below.

[Patent Document 1] Japanese Patent Kohyo* Publication No. 2003-535965 (*unexamined Japanese national phase publication corresponding to a non-Japanese international publication)

[Patent Document 2] Japanese Patent Kohyo Publication No. Hei 10-50347

[Patent Document 3] Japanese Patent Kokai No. Hei 10-295371 (unexamined, published Japanese patent application)

[Non-Patent Document 1] Karlson, K. A. Animal glycosphingolipids as membrane attachment site for bacteria. Ann. Rev. Biochem. 58, 309-350, 1989

[Non-Patent Document 2] Cohen A, Hannigan G E, Williams B R, Lingwood C A. J Biol Chem. 1987 Dec 15;262(35): 17088-91. Roles of globotriosyl- and galabiosylceramide in verotoxin binding and high affinity interferon receptor.

[Non-Patent Document 3] Lindberg A A, Brown J E, Stromberg N, Westling-Ryd M, Schultz J E, Karlsson K A. J Biol Chem. 1987 Feb 5;262(4):1779-85. Identification of the carbohydrate receptor for Shiga toxin produced by *Shigella dysenteriae* type 1.

[Non-Patent Document 4] Stromberg N, Deal C, Nyberg G, Normark S, So M, Karlsson K A. Proc Natl Acad Sci U S A. 1988 Jul;85(13):4902-6. Identification of carbohydrate structures that are possible receptors for *Neisseria gonorrhoeae*.

[Non-Patent Document 5] Stromberg N, Ryd M, Lindberg A A, Karlsson K A. FEBS Lett. 1988 May 9;232(1):193-8. Studies on the binding of bacteria to glycolipids. Two species of Propionibacterium apparently recognize separate epitopes on lactose of lactosylceramide.

[Non-Patent Document 6] Voelker, T. A. et al.: Fatty acid biosynthesis redirected to medium chains in transgenic oilseed plants, Science, 257, 72-74(1992)

[Non-Patent Document 7] Sayanova, O. et al.: Expression of a borage desaturase cDNA containing and N-terminal cytochrome b5 domain results in the accumulation of high levels of Δ6-desaturated fatty acids in transgenic tobacco, Proc. Natl. Acad. Sci. U.S.A., 94, 4211-4216(1997)

[Non-Patent Document 8] Ye, X. et al.: Engineering the provitamin A (β-carotene) biosynthetic pathway into (carotenoid-free) rice endosperm, Science, 287, 303-305(2000)

[Non-Patent Document 9] Datta, K.: Bioengineered 'golden' indica rice cultivars with β-carotene metabolism in the endosperm with hygromycin and mannose selection systems, Plant Biotech. J., 1, 81-90(2003)

[Non-Patent Document 10] Tozawa, Y et al.: Characterization of rice anthranilate synthase a-subunit genes OASA1 and OASA2. Tryptophan accumulation in transgenic rice expressing a feedback-insensitive mutant of OASA1, Plant Physiology, 126, 1493-1506(2001)

[Non-Patent Document 11] Nirianne Q. Palacpac et al., Stable expression of human β1,4-galactosyltransferase in plant cells modifies N-linked glycosylation patterns, Proc. Natl. Acad. Sci. USA, 96, 4692-4697 (1999)

[Non-Patent Document 12] Watarai, S. et al., Inhibition of vero cell cytotoxic activity in *Escherichia coli* O157:H7 lysates by globotriaosylceramide, Gb3, from bovine milk. Biosci. Biotechnol. Biochem. 65, 414-419 (2001).

[Non-Patent Document 13] Hasegawa, A., Morita, M., Kojima, Y., Ishida, H. & Kiso, M., Synthesis of cerebroside, lactosylceramide, and ganglioside GM3 analogs containing β-thioglycosidically linked. Carbohydr. Res. 214, 43-53 (1991).

[Non-Patent Document 14] N. Strömberg et al. (1988) Two species of Propionibacterium apparently recognize separate epitopes on lactose of lactosylceramide FEBS Lett. 232, 193-198.

[Non-Patent Document 15] K. Furukawa and T. Sato (1999) β-1,4-Galactosylation of N-glycans is a complex process. Biochim. Biophys. Acta. 1473, 54-66.

[Non-Patent Document 16] M. Amado et al. (1999) Identification and characterization of large galactosyltransferase gene families: galactosyltransferase for all functions. Biochi. Biophys. Acta. 1473, 35-53.

[Non-Patent Document 17] Harwood, J. L. (1998) What's so special about plant lipids? In Plant Lipid Biosynthesis, ed. Harwood, J. L., 1-26. Cambridge University Press.

[Non-Patent Document 18] Shimojima, M., Ohta, H., Iwamatsu, A., Masuda, T., Shioi, Y., and Takamiya, K. (1997) Cloning of the gene for monogalactosyldiacylglycerol synthase and its evolutionary origin. Proc. Natl. Acad. Asi. USA. 94, 333-337.

[Non-Patent Document 19] Miego, C., Marechal, E., Shimojima, M., Block, M. A., Ohta, H., Takamiya, K., Douce, R., and Joyard, J. (1999) Biochemichal and topological properties of type A MGDG synthase, a spinach chloroplast envelope enzyme catalyzing the synthesis of both prokaryotic and eukaryotic MGDG Eur. J. Biochem. 365, 990-1001.

[Non-Patent Document 20] Kelly, A. A., Froehlich, J. E., and Dörmann, P. (2003) Disruption of the two digalactosyldiacylglycerol synthase genes DGD1 and DGD2 in Arabidopsis reveals the existence of and additional enzyme of galactolipid synthesis. Plant Cell, 15, 2694-2706.

[Non-Patent Document 21] Bligh, E. G. and Dyer, W. J. (1959) A rapid method of total lipid extraction and purification. Can. J. Biochem. Physiol. 37, 911-917.

[Non-Patent Document 22] Francois, C., Marshall, R. D., and Neuberger, A. (1962) Carbonhydrates in protein. 4. The determination of mannose in hen's-egg albumin by radio-isotope dilution. Biochem. J., 83, 335-341.

[Non-Patent Document 23] Ohnishi, M., Ito, S., and Fujino, Y. (1983) Characterization of sphingolipids in spinach leaves. Biochim. Biophys. Acta., 752, 416-422.

[Non-Patent Document 24] Lynch, D. V. (1993) in Lipid metabolism in plants. Sphingolipids. CRC press, 285-308.

[Non-Patent Document 25] Kelly, A. A., and Dörmann, P. (2004) Green light for galactolipid trafficking. Curr. Opinions Plant Biol., 7, 262-269.

[Non-Patent Document 26] Imai, H., Ohnishi, M., Kinoshita, M., Kojima, M., and Ito, S. (1995) Structure and distribution of cerebroside containing unsaturated hydroxyl fatty acids in plant leaves. Biosci. Biotech. Biochem., 59, 1309-1313.

[Non-Patent Document 27] Sanders, P. R., Winter, J. A., Barnason, A. R., Rogers, S. G., and Fraley, R. T. (1984) Comparison of cauliflower mosaic virus 35S and nopaline synthase promoters in transgenic plants. Nucleic Acid Res., 15, 1543-1558.

[Non-Patent Document 28] Trinchera, M., Fiorilli, A., and Ghidoni, R. (1991) Localyzation in the golgi apparatus of rat liver UDP-Gal:glucosylceramide β1,4-galactosyltransferase. Biochemistry, 30, 2719-2724.

DISCLOSURE OF THE INVENTION

Problems to be Solved by the Invention

The present invention was completed in view of the above circumstances. An objective of the present invention is to provide methods for mass-producing lactosylceramide, an animal-specific glycolipid, in safe conditions free from the risk of animal-derived infectious diseases. Specifically, an objective of the present invention is to provide genetically modified plants having the capability to produce lactosylceramide and methods for producing lactosylceramide by using these plants.

Means for Solving the Problems

To solve the above problems, the present inventors attempted to produce lactosylceramide by introducing a cDNA of human β1,4-galactosyltransferase gene (β1,4GT) into tobacco. However, the transformed tobacco comprising introduced β1,4GT produced no or a very small amount of lactosylceramide. Thus, the present inventors tried to produce lactosylceramide by introducing an isoform gene of human-derived β1,4-galactosyltransferase (β1,4GT5) into tobacco.

As a result, lactosylceramide was detected in the leaves of selected recombinant tobacco, and the amount thereof was found to be as large as 200 μg or more per 1 g of fresh recombinant tobacco leaves (about 2000 times of that by a conventional method). That is, mass synthesis of lactosylceramide in recombinant plants became possible through the introduction of human β1,4GT5 (FIG. 7). In more detail, the present invention provides [1] to [7] below.

[1] A vector comprising a human-derived DNA operably linked downstream of a promoter region expressible in plant cells, wherein the DNA is any one of the following (a) to (c):
(a) a DNA encoding a protein comprising the amino acid sequence described in SEQ ID NO: 2;
(b) a DNA comprising a coding region of the nucleotide sequence described in SEQ ID NO: 1; and
(c) a DNA encoding a protein comprising an amino acid sequence with one or more amino acid substitutions, deletions, additions, and/or insertions in the amino acid sequence described in SEQ ID NO: 2.

[2] A transformed plant cell introduced with the vector of [1].

[3] A plant having a capability of producing lactosylceramide, wherein the plant is regenerated from the transformed plant cell of [2].

[4] A plant having a capability of producing lactosylceramide, wherein the plant is a progeny or clone of the plant of [3].

[5] A propagation material of the plant of [3] or [4], wherein the plant has a capability of producing lactosylceramide.

[6] A method of producing a plant having a capability of producing lactosylceramide, wherein the method comprises:
(i) introducing the vector of [1] into a plant cell; and
(ii) regenerating a plant from the transformed plant cell introduced with the vector in step (i).

[7] A method of producing lactosylceramide, wherein the method comprises using the transformed plant cell of [2], the plant of [3] or [4], or the propagation material of [5]. Furthermore, the present invention provides [8] to [10] below.

[8] A method of producing lactosylceramide comprising at least the processes (i) to (iii) below:
(i) introducing the vector of [1] into a plant cell;
(ii) regenerating a plant from a transformed plant cell into which the vector has been introduced in process (i); and
(iii) extracting and purifying lactosylceramide from the plant regenerated in process (ii).

[9] A composition for producing lactosylceramide comprising as an active ingredient the transformed plant cell of [2], the plant of [3] or [4], or the propagation material of [5].

[10] Use of the transformed plant cell of [2], the plant of [3] or [4], or the propagation material of [5], in the manufacture of lactosylceramide.

BEST MODE FOR CARRYING OUT THE INVENTION

Figure 1:
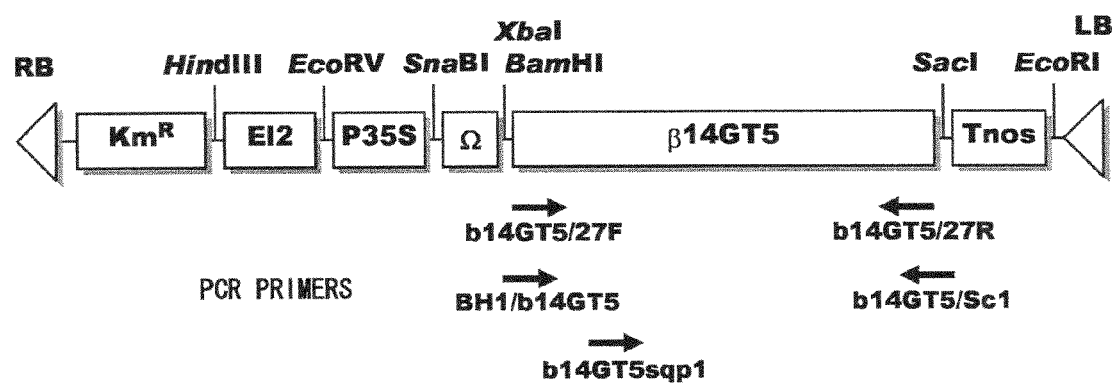
FIG. 1 is a diagram showing the T-DNA region of pBE/b14GT5. $Km^R$ indicates a kanamycin-resistant neomycin phosphotransferase gene. E12 indicates a sequence in which two 5'-upstream regions (from −419 to −90) of the cauliflower mosaic virus (CaMV) 35S promoter are linked, and P35S indicates a 5' upstream region (from −90 to −1) of the CaMV 35S promoter. Ω sequence is a 5' upstream region of tobacco mosaic virus. Tnos indicates a nopaline synthase polyadenylation region.

The present invention provides vectors that can be expressed in plant cells, comprising a coding region of an isoform gene (β1,4GT5) of the human-derived β1,4-galactosyltransferase. Specifically, the present invention provides vectors in which a human-derived β1,4GT5-encoding DNA is operably linked downstream of a promoter region that can be expressed in plant cells. The sequence of the β1,4GT5 cDNA is shown in SEQ ID NO: 1 and the protein synthesized by the DNA is shown in SEQ ID NO: 2.

Here, "operably linked to" means that a human-derived β1,4GT5-encoding DNA is linked downstream of a promoter region capable of being expressed in plant cells, so that expression of a DNA encoding human-derived β1,4GT5, which is a foreign gene, can be induced in plant cells.

A coding region of β1,4GT5 comprised in the vectors of the present invention is preferably a cDNA sequence of β1,4GT5. cDNA preparation can be carried out by those skilled in the art using common practice. For example, a cDNA of β1,4GT5 can be obtained by designing an appropriate pair of primers based on known information of the β1,4GT5 nucleotide sequence, carrying out PCR using mRNA prepared from human as template, and screening a cDNA library by using the amplified DNA fragments as probes. Furthermore, the DNA of interest can also be prepared synthetically by using a commercially available DNA synthesizer.

As a DNA comprised in the vectors according to the present invention, DNAs encoding a protein that is structurally similar to human-derived β1,4GT5 (SEQ ID NO: 2) (for example, mutants, derivatives, alleles, variants, and homologues) can also be used, as long as the protein has the capability to act on glucosylceramide and synthesize lactosylceramide via a sugar transfer reaction. Such DNAs include, for example, DNAs coding for proteins comprising an amino acid sequence with one or more amino acid substitutions, deletions, additions and/or insertions in the amino acid sequence of SEQ ID NO: 2.

It is already known that a protein having an amino acid sequence modified by deletion, addition, and/or substitution of one or more amino acid residues in an amino acid sequence with other amino acids can maintain its biological function (activity) (Mark, D. F. et al., Proc. Natl. Acad. Sci. USA (1984) 81, 5662-5666, Zoller, M. J. & Smith, M. Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413).

Methods well known to those skilled in the art for preparing a DNA that encodes a protein with modified amino acid sequence include, for example, a site-directed mutagenesis method (Kramer, W. & Fritz, H.-J. (1987) Oligonucleotide-directed construction of mutagenesis via gapped duplex DNA. Methods in Enzymology, 154: 350-367). Methods for introducing mutations into a protein's amino acid sequence include, for example, a site-directed mutagenesis method (Current Protocols in Molecular Biology, edit. Ausubel et al. (1987), Publish. Jhon Wily & Sons, Sections 8.1-8.5). In addition, a protein's amino acid sequence may mutate naturally as a result of mutations in the nucleotide sequence encoding the protein. The DNAs of the present invention also include DNAs that encode proteins which have an amino acid sequence with one or plural amino acid substitutions, deletions, or additions in an amino acid sequence encoding the natural-type β1,4GT5 (SEQ ID NO: 2), as long as they encode proteins having a function equivalent to that of the natural-type protein.

Here, "having a function equivalent to" means that the subject protein has, for example, a biological function (activity) equivalent to that of a protein comprising the β1,4GT5-encoding amino acid sequence. The present invention implies that the subject protein has, for example, the capability to act on glucosylceramide and synthesize lactosylceramide via a sugar transfer reaction.

As long as the modified protein has the capability to act on glucosylceramide and synthesize lactosylceramide via a sugar transfer reaction, the number of amino acids to be modified is not specifically limited, and it is generally within 50 amino acids, preferably within 30 amino acids, and more preferably within 10 amino acids (for example, within 5 amino acids or within 3 amino acids). The amino acid modification is preferably conservative substitutions. The numerical values for the hydropathic index (Kyte and Doolitte, (1982) J Mol Biol. 1982 May 5; 157(1):105-32) or hydrophilicity value (U.S. Pat. No. 4,554,101) before and after modification are preferably within ±2, more preferably within ±1, and most preferably within ±0.5.

Mutations in a nucleotide sequence may not be accompanied by mutations in the protein's amino acid sequence (degenerative mutations). Such degenerative mutants are also included in the DNAs of the present invention.

As for the type of amino acid residues to be modified, it is preferable that amino acids are modified into those that conserve the nature of the amino acids before modification (amino acids similar to those before modification). The nature of amino acid side chains can be exemplified by hydrophobic amino acids (A, I, L, M, F, P, W, Y, V), hydrophilic amino acids (R, D, N, C, E, Q, G, H, K, S, T), amino acids comprising an aliphatic side chain (G, A, V, L, I, P), amino acids comprising a hydroxy-containing side chain (S, T, Y), amino acids comprising a sulfur-containing side chain (C, M), amino acids comprising a carboxylic acid- or amide-containing side chain (D, N, E, Q), amino acids comprising a base-containing side chain (R, K, H), and amino acids comprising an aromatic-containing side chain (H, F, Y, W) (letters in parentheses refer to amino acids in single-letter notation).

Also included in the above-mentioned DNAs, which encode proteins comprising an amino acid sequence with multiple amino acid additions to the β1,4GT5-encoding amino acid sequence, are DNAs which encode fusion proteins comprising such proteins. Such fusion proteins comprise a protein comprising a β1,4GT5-encoding amino acid sequence and a protein comprising a different amino acid sequence. The method of fusion protein production can be any method, as long as it can link a DNA coding for the above-mentioned β1,4GT5 with a DNA that encodes a different protein in a manner that their frames match, insert the resultant DNA into an expression vector, and express it in a host. Techniques known to those skilled in the art can be used. There are no specific limitations on the protein to be fused with a protein comprising a β1,4GT5-encoding amino acid sequence.

The protein to be fused with a protein comprising a β1,4GT5-encoding amino acid sequence can be selected appropriately according to various purposes such as protein purification and/or isolation and application research. For example, it is possible to use known proteins such as FLAG (Hopp, T. P. et al., BioTechnology (1988) 6, 1204-1210), 6× His consisting of six His (histidine) residues, 10× His, influenza virus hemagglutinin (HA), human c-myc fragments, VSV-GP fragments, p18HIV fragments, T7-tag, HSV-tag, E-tag, SV40 T-antigen fragments, lck tag, α-tubulin fragments, B-tag, Protein C fragments, and such. The proteins to be fused with a protein comprising β1,4GT5-encoding amino acid sequence also include, for example, GST (glutathione-S-transferase), HA (influenza virus hemagglutinin), immunoglobulin constant regions, β-galactosidase, MBP (maltose-binding protein), and such. Fusion proteins can be prepared by expressing fusion DNAs, which are prepared by fusing a DNA encoding a commercially available protein with a β1,4GT5-encoding DNA.

The above-mentioned β1,4GT5-encoding amino acids include those that have not been modified from the state in nature and those that have been modified. The modifications include acetylation, acylation, ADP-ribosylation, amidation, covalent binding of a flavin, covalent binding of a heme moiety, covalent binding of a nucleotide or a nucleotide derivative, covalent binding of a lipid or a lipid derivative, covalent binding of a phosphatidylinositol, cross-bridging, cyclization, disulfide bond formation, methylation, demethylation, covalent cross-bridge formation, cystine formation, pyroglutamate formation, formylation, γ-carboxylation, glycosylation, GPI-anchor formation, hydroxylation, iodination, myristoylation, oxidation, protein decomposition treatment, phosphorylation, prenylation, racemization, selenoylation, sulfation, transfer-RNA mediated addition of amino acids to proteins such as arginylation, ubiquitination, and such.

Other methods known to those skilled in the art for preparing a protein that has a function equivalent to a certain protein are, for example, methods utilizing hybridization techniques (Sambrook, J et al., Molecular Cloning 2nd ed., 9.47-9.58, Cold Spring Harbor Lab. press, 1989). Namely, by using the above-mentioned β1,4GT5-encoding DNAs or parts thereof, those skilled in the art can readily isolate DNAs hat have high homologies with these DNAs, from DNA samples derived from various organisms (for example, human) or from artificially synthesized nucleotide libraries and such, and isolate proteins having a function equivalent to a protein comprising a β1,4GT5-encoding amino acid sequence by using the isolated DNAs.

The present invention's DNAs include DNAs that hybridize with a DNA encoding a protein comprising the amino acid sequence of SEQ ID NO: 2 according to the present invention and which encode a protein having a function equivalent to that of a protein comprising the amino acid sequence of SEQ ID NO: 2.

Those skilled in the art can appropriately choose hybridization conditions to isolate a DNA that encodes a protein having a function equivalent to a protein comprising the amino acid sequence of SEQ ID NO: 2. Hybridization conditions include, for example, low stringent conditions. Low stringent conditions are, for example, conditions of "42° C., 0.1×SSC, 0.1% SDS", and preferably conditions of "50° C., 0.1×SSC, 0.1% SDS" during the washing step following hybridization. More preferable hybridization conditions include conditions of high stringency. Conditions of high stringency are, for example, conditions of "65° C., 5×SSC, and 0.1% SDS". Under these conditions, increasing the temperature is expected to efficiently obtain DNAs with a higher homology. However, multiple factors such as temperature and salt concentration are considered to affect hybridization stringency, and those skilled in the art can achieve a similar stringency by appropriately choosing these conditions.

Instead of hybridization, a gene-amplification technique (PCR) (Current protocols in Molecular Biology edit. Ausubel et al. (1987) Publish. John Wiley&Sons Section 6.1-6.4) can also be used to design primers based on a part of a DNA encoding a protein comprising the amino acid sequence of SEQ ID NO: 2, isolate DNA fragments having a high homology with this DNA, and obtain a DNA which encodes a protein having a function equivalent to that of a protein comprising the amino acid sequence of SEQ ID NO: 2 based on the thus-isolated DNA.

The proteins encoded by the DNAs isolated using the above-mentioned hybridization or gene-amplification technique and having an equivalent function with a protein comprising the amino acid sequence of SEQ ID NO: 2 usually have high amino acid sequence homologies with a protein comprising the amino acid sequence of SEQ ID NO: 2. In the present invention, the DNAs encoding a protein comprising the amino acid sequence of SEQ ID NO: 2 include DNAs encoding a protein that has a function equivalent to that of a protein comprising the amino acid sequence of SEQ ID NO: 2 and which has a high amino acid sequence homology with the protein comprising the amino acid sequence of SEQ ID NO: 2. "High homology" usually means at least 50% or more, preferably 75% or more, more preferably 85% or more, even more preferably 95% or more (for example, 96% or more, 97% or more, 98% or more, or 99% or more) identity at the amino acid sequence level. Protein homology can be determined by following the algorism described in the literature (Wilbur, W. J. and Lipman, D. J. Proc. Natl. Acad. Sci. USA (1983) 80, 726-730).

Amino acid sequence identity can be determined, for example, by using the algorism BLAST by Karlin and Altschul (Proc. Natl. Acad. Sci. USA 87:2264-2268, 1990, Proc. Natl. Acad. Sci. USA 90:5873-5877, 1993). A program called BLASTX has been developed based on this algorism (Altschul et al. J. Mol. Biol. 215: 403-410, 1990). When an amino acid sequence is analyzed using BLASTX, parameters are set to, for example, score=50 and wordlength=3. When the BLAST and Gapped BLAST programs are used, default parameters of each program are used. Specific techniques of these analytical methods are already known (http://www.ncbi.nlm.nih.gov).

One can judge whether or not a protein encoded by a certain DNA "has the capability to act on glucosylceramide and synthesize lactosylceramide via a sugar transfer reaction" by knowing whether or not plant cells introduced with a vector comprising a DNA encoding the mutant protein can synthesize lactosylceramide from endogenous glucosylceramide. As an example, one can make the above judgment by knowing whether lactosylceramide is detected or not in a plant regenerated from cells to which a DNA encoding the protein has been introduced, as shown in Examples 6-10.

The vectors of the present invention are not specifically limited as long as they comprise a promoter region that enables the expression of a foreign gene in plant cells. Examples of a promoter used for carrying out continuous gene expression in plant cells are the cauliflower mosaic virus (CaMV) 35S promoter (for example, Odel et al, Nature,313: 810, 1985; Dekeyser et al, Plant Cell, 2:591, 1990; Terada and Shimamoto, Mol. GeN. Genet. 220:389, 1990; and Benfey and Chua, Science, 250:959-966, 1990), nopaline synthase promoter (An et al., Plant Physiol. 88:547, 1988), octopine synthase promoter (Fromm et al., Plant Cell, 1:977,1989), and 2× CaMV/35S promoter with translational enhancer sequence (Kay et al Science, 236:1299-1302, 1987).

Promoters that are inducibly activated by external stimulation can also be used for the expression of foreign genes in plant cells. Examples of such promoters are: (a) heat-inducible promoters by (Callis et al., Plant Physiol., 88:965,1988; Ainley et al., Plant Mol. Biol., 22:13-23, 1993; and Gilmartin et al., The Plant Cell, 4:839-949, 1992); (b)light-inducible promoters (for example, the pea rbcS-3A promoter, Kuhlemeier et al., Plant Cell, 1:471, 1989; and the maize rbcS promoter, Schaffner and Sheen, Plant Cell, 3:997, 1991); (c) hormone-inducible promoters (for example, abscisic acid-inducible promoters, Marcotte et al., Plant Cell. 1:471, 1989), (d) wound-inducible promoters (for example, the potato PinII promoter, Keil et al., Nucl. Acids. Res. 14: 5641-5650, 1986; the *Agrobacterium* mas promoter, Langridge et al., Bio/Technology 10:305-308, 1989; and the grape vst1 promoter, Weise et al., Plant Mol. Biol., 26:667-677,1994), and (e) promoters inducible by chemical substances such as methyl jasmonate or salicylic acid (Gatz et al., Plant Mol. Biol. 48:89-108, 1997).

Ubiquitin promoters, soybean chlorotic mottle virus promoters, retrotransposon promoters, LHCPII promoters, and such are also usable.

The insertion of genes into vectors can be carried out by conventional methods, for example, by ligase reactions using restriction enzyme sites (Current protocols in Molecular Biology edit. Ausubel et al. (1987) Publish. John Wiley & Sons. Section 11.4-11.11).

The vectors of the present invention can also include, for example, an RNA-processing signal such as an intron located upstream or downstream of the coding region of β1,4GT5. They can also include an additional control sequence derived from a plant gene's 3'-end untranslated region, such as a 3'-end terminator region, to enhance mRNA stability. Examples include potato PI-II terminator regions, and 3'-end terminator regions of octopine synthase or nopaline synthase.

Furthermore, the vectors of the present invention can comprise a dominant selection marker gene to enable quick selection of transformants. Dominant selection marker genes include antibiotic-resistant genes (for example, resistance to hygromycin, kanamycin, bleomycin, G418, streptomycin, or spectinomycin) and herbicide-resistant genes (for example, phosphinothricin acetyltransferase gene).

The types of plant cells into which the above-mentioned vectors are introduced are, preferably tobacco, wheat, rice, maize, adzuki bean, konjac, and such; however, the cells are not limited to these plant cells as long as they can synthesize lactosylceramide inside and are transformable.

The vectors of the present invention can be introduced into plant cells by methods known to those skilled in the art. For instance, introduction into tobacco can be carried out by methods such as the *Agrobacterium* transformation method described in the Examples, particle gun methods, electroporation methods, methods of monocotyledon transformation using *Agrobacterium*, polycation methods, methods of plant protoplast transformation (polyethylene-glycol methods), calcium-phosphate precipitation methods, Lipofectamine methods (GIBCO-BRL), and microinjection methods. The *Agrobacterium* methods can be used for gene introduction into rice (Hiei Y et al., Plant Mol Biol. Sep; 35(1-2): 205-218), barley (Higuchi K et al., Plant J Jan;25(2):159-167), rapeseed (Damgaard O & Rasmussen O et al., Plant Mol Boil 1991 Jul;17(1) 1-8), potato (Yu J. & Langridge W., Transgenic Res. 2003 Apr, 12 (2): 163-169), asparagus (Ignacimuthu S., Indian J. Exp. Biol. 2000 May;38(5):493-498), eggplant (Rotino G L et al, Nat. Biotechnol. 1997 Dec; 15(13): 1398-1401), red pepper (Shin R. et al., Transgenic Res. 2002 Apr; 11(2): 215-219), tomato, sweet potato, melon (for these three species; Mihalka V. et al., Plant Cell Rep. 2003 Apr;21(8): 778-784), soybean (Zeng P et al., Plant Cell Rep. 2004 Feb; 22(7) 478-482), sugarcane (Manickavasagam M. et al, Plant Cell Rep. 2004 May 5), sorghum (Zhao ZY et al., Plant Mol. Biol. 2000 Dec;44(6): 789-798), buckwheat (Kojima M. et al., Biosci. Biotechnol. Biochem. 2000 Apr;64(4):845-847), carrot (Koyama H. et al., Plant Cell Physiol. 1999 May;40(5): 482-484), apple (Szankowski I. et al., Plant Cell Rep. 2003 Sep;22(2):141-149), and such. The electroporation or particle gun methods can be used for gene introduction into rice (Shimamoto K. et al, Nature 338, 274-276 (1989)), corn (Kyozuka J. et al., Mol Gen Genet. Aug; 228(1-2): 40-48), and such. The particle gun method can be used for gene introduction into banana (Sagi L. et al., Biotechnology (NY). 1995 May;13(5):481-485), rye (Popelka J C et al., Transgenic Res. 2003 Oct;12(5):587-596), and such.

The present invention provides transformed plant cells into which the above-mentioned vector has been introduced. The transformed plant cells of the present invention can be in any form as long as they are plant cells or a group of plant cells into which the above-mentioned vector has been introduced and that have the capability of producing lactosylceramide. The cells are those that have the ability to regenerate plant bodies for production of transformed plants. For example, cells cultured in a liquid medium, protoplasts, leaf sections, callus, and such are included in the plant cells of the present invention.

The present invention provides plants (plant bodies) which are regenerated from the above-mentioned transformed cells and have the capability to produce lactosylceramide. According to the present invention, "plants (plant bodies) having the capability to produce lactosylceramide" refers to plants that have been modified to synthesize lactosylceramide, which is normally not synthesized in plants, from endogenous glucosylceramide via a sugar transfer reaction.

The synthesis of animal sphingoglycolipids (glycolipids of ganglio-, globo-, and lacto-series) in plants becomes possible by introducing into the present invention's transformed plants, which are already introduced with human-derived β1,4GT5, genes encoding enzymes involved in the biosynthetic route from lactosylceramide to sphingoglycolipids, and then adding sugars to lactosylceramide in the plants (see FIG. 3-18 "Major biosynthetic routes of sphingoglycolipids" in Hitoo Iwase et al., Baifukan, "An Introduction of Sugar Chain Science (Tou-sa no Kagaku Nyu-mon)" pp. 65). The enzymes for synthesizing ganglio-series sphingoglycolipids include α2,3-sialyltransferase and β1,4-N-acetyl-galactosaminyltransferase; those for synthesizing globo-series sphingoglycolipids include α1,4-galactosyltransferse; and those for synthesizing lacto-series sphingoglycolipids include β1,3-N-acetylglucosaminyltransferase. According to the present invention, "plants having the capability to produce lactosylceramide" include transformed plants that are introduced with, in addition to human-derived β1,4GT5, a gene encoding an enzyme involved in the biosynthetic route from lactosylceramide to sphingoglycolipids in animals.

The present invention provides not only plants regenerated from cells introduced with the above-described vectors but also their progenies and clones. Once a transformed plant comprising the above-mentioned vector in its genome is obtained, progenies or clones can be obtained from the plant by sexual or asexual reproduction. Materials for propagation (for example, seeds, fruits, ears, tubers, root tubers, stumps, callus, protoplasts, and such) can also be obtained from the plant and or its progenies or clones to mass-produce the plant from such materials.

Furthermore, the present invention provides methods for producing a plant having the capability to produce lactosylceramide. The present methods comprise the steps of introducing the above-mentioned vector into a plant cell and regenerating a plant from the cell introduced with the vector.

The step of regenerating a plant from transformed plant cells can be carried out by methods known to those skilled in the art depending on plant species. For example, as described in Example 3, in the case of tobacco, transformed tobacco shoots can be obtained by infecting tobacco leaves with the above-mentioned vector by a leaf disc method, washing them with an MS liquid medium containing the antibiotics kanamycin and carbenicillin to remove bacteria used for the infection, and then culturing the leaves on a re-differentiation MS agar medium containing the antibiotics. Generally, a dominant selection marker incorporated into a transformation vector confers the shoots of a transformed plant antibiotic resistance; thus, transformants can be selected by exposing shoots to appropriate concentrations of antibiotics. In addition to kanamycin, antibiotics used for the transformant selection include hygromycin and such. Other selection methods include the MAT vector method and such.

Furthermore, the present invention provides methods of lactosylceramide production comprising using the above-mentioned transformed plant cells or transformed plants. Recovery of lactosylceramide from plant cells or plants can be carried out by methods known to those skilled in the art.

In the present invention, an embodiment of a lactosylceramide production method is a method that comprises the following steps (i) to (iii):

(i) introducing a vector of the present invention into a plant cell;
(ii) regenerating a plant from the transformed plant cell into which the vector has been introduced in step (i); and
(iii) extracting and purifying lactosylceramide from the plant regenerated in step (ii).

For example, the step of culturing transformed plant cells comprising a vector of the present invention and recovering lactosylceramide from the culture supernatants thereof is also included in the present invention.

Further, an example of a method of extracting lactosylceramide from tobacco is described below.

First, total lipid is extracted from plant bodies with chloroform/methanol. Specifically, 5-10 g tobacco leaves are soaked in 100 ml of chloroform:methanol (1:2 in volume ratio), homogenized with a Polytron homogenizer for about two minutes, and the resultant homogenate is filtrated through four layers of Miracloth. The homogenate is transferred to a separatory funnel, and chloroform and water were added to make the volume ratio of chloroform:methanol:water 1:1:0.9. The lower layer of the two separated layers is collected and concentrated with a rotary evaporator to complete total lipid extraction.

Next, sphingolipids are obtained from the total lipid fraction by weak alkaline degradation. Specifically, a portion of the total lipid obtained by the above-described method (about 0.5 ml; containing 0.8 g of total lipid) is mixed with 30 ml of methanol containing 0.4 M KOH, and the mixture is allowed to react at 37° C. for two hours. During this reaction, only glycerolipids are decomposed while sphingolipids are not. The reaction mixture is transferred to a separatory funnel, and 30 ml of chloroform and 27 ml of water are added thereto. After mixing, the lower layer of the two separated layers is collected and concentrated with a rotary evaporator to give a sphingolipid fraction.

Finally, lactosylceramide is purified using a silica-gel column. Specifically, a glass chromatography column with an inside diameter of 2 cm is packed to a height of 1.5 cm with silica gel (Iatrobeads or Iatron 6RS-8060). Sphingolipids dissolved in 0.5 ml of chloroform:methanol (90:10) are loaded onto the column and gradiently eluted by changing the ratio of the chloroform:methanol solution from (90:10) to (70:30). Pigments and glucosylceramide are first eluted, and then lactosylceramide is eluted (about 80:20).

The lactosylceramide obtained by the above methods is also included in the present invention.

The present invention also provides compositions for producing lactosylceramide, which comprise as an active ingredient the present invention's transformed plant cell or transformed plant. The compositions can further comprise, without specific restriction, physiologically acceptable substances that can stably maintain the shape of the transformed plant cells or transformed plants. For example, they can comprise water, inorganic salts, amino acids, sugar-containing solutions, culture media, or buffers and such.

The present invention further provides the use of the present invention's transformed plant cells or transformed plants in lactosylceramide production.

Next, the present invention will be specifically described using Examples; however, it is not to be construed as being limited thereto.

EXAMPLE 1

A method for Isolating an Isoform Gene (β1,4GT5) of Human-Derived β1,4-galactosyltransferase A first-strand cDNA was synthesized by reverse transcription using polyA+ mRNA (STRATAGENE) derived from human heart as template and oligo dT primers. The CDNA was used as a template in the PCR method to amplify a full-length ORF (1,167 bp) of β1,4GT5 (Accession No. NM_004776 (NCBI)). In the PCR, β14GT5/27F (5'-AT-GCGCGCCCGCCGGGGGCTGCTGCGG-3'/SEQ ID NO: 3) and β1,4GT5/27R (5'-TCAGTACTCGTTCACCTGAGC-CAGCTC-3'/SEQ ID NO: 4) were used as primers. For PCR reactions, KOD Plus DNA polymerase (TOYOBO), which causes few errors, was used. After a 2-minute treatment at 94° C., a PCR cycle of 15 seconds at 94° C. and two minutes at 68° C. was repeated 35 times. The resultant single band was inserted into the EcoRV site of the pBluescript II KS+ plasmid, and a pBS/β14GT5 clone was obtained. The sequence of the cDNA clone was confirmed by checking the restriction enzyme sites and by sequencing using ABI PRISM Big Dye Terminator Ver3 (Applied Biosystems, California, USA).

The DNA sequence and amino acid sequence of human β1,4GT5 are shown in SEQ ID NO: 1 and SEQ ID NO: 2, respectively.

EXAMPLE 2

Construction of a Plant Expression Vector for Human-Derived β1,4GT5

The Ti-plasmid vector pBE2113 was digested with restriction enzymes BamHI and SacI and separated by electrophoresis to give pBE2113ΔGUS fragments in which the GUS cartridge was removed. To insert pBS/β14GT5 into the fragments, PCR was carried out to add BamHI and SacI sites. The reaction was carried out under the same conditions as mentioned above by using BH1/b14GT5 (5'-TTG GGATC-CATGCGCGCCCGCCGGGGGGG/SEQ ID NO: 5) and b14GT5/Sc1 (5'-AAGGAGCTCTCAGTACTCGTTCAC-CTGAGC/SEQ ID NO: 6) as primers. After the resultant PCR products were digested with BamHI and SacI, the fragments were ligated with the pBE2113ΔGUS fragment to construct the plant expression vector pBE/βGT5. This clone was sequenced in the same way as mentioned above, and confirmed to have no errors The expression vector has a structure in which expression of the inserted β1,4GT5 cDNA is regulated under the cauliflower mosaic virus 35S promoter (35S), Ω sequence, and nopaline synthase terminator (NOS). The vector also contains kanamycin-resistant gene as a marker for transformant selection.

The plant expression vector of human β1,4GT5 is shown in FIG. 1.

EXAMPLE 3

Tobacco Transformation

The transformation of tobacco (Nicotiana tabacum cv. Blight Yellow) was carried out by a leaf disc method using Agrobacteriun. Leaf discs of about 1 cm on each side were excised from leaves of aseptically cultivated tobacco, and infected by soaking in a suspension of Agrobacterium tumefacience LBA4404 strain carrying pBE/GT5 and coculturing on an MS agar culture medium for two days. On day 3, Agrobacterium bodies were removed by washing the leaf discs with an MS liquid medium containing 50 mg/l kanamycin and 500 mg/l carbenicillin, and then transformed tobacco shoots were obtained by cultivating the leaf discs on a redifferentiation MS agar medium containing the antibiotics.

EXAMPLE 4

Genomic DNA Analysis of the Recombinant Tobacco Introduced With β1,4GT5

PCR was carried out to confirm that human β1,4GT5 was inserted into the tobacco chromosomal genome. For each of the 62 recombinant tobacco strains with confirmed kanamycin resistance, DNA was extracted (DNeasy Plant Mini Kit, QIAGEN) from about 0.1 g leaf, and PCR was carried out by using a portion of the DNA as template. To cover the full-length ORF of β1,4GT5, b14GT5/27F (5'-ATGCGCGC-CCGCCGGGGGCTGCTGCGG/SEQ ID NO: 3) and b14GT5/27R (5'-TCAGTACTCGTTCACCTGAGC-CAGCTC/SEQ ID NO: 4) were used as primers. For PCR, TAKARA EX Taq polymerase was used, and a cycle of 30 seconds at 94° C., 30 seconds at 65° C., and 1.5 minutes at 72° C. was repeated 40 times. All the 16 clones examined showed iso-type β1,4-galactosyltransferase-specific bands, confirming that the gene is indeed inserted in the nuclear genome.

Figure 2:
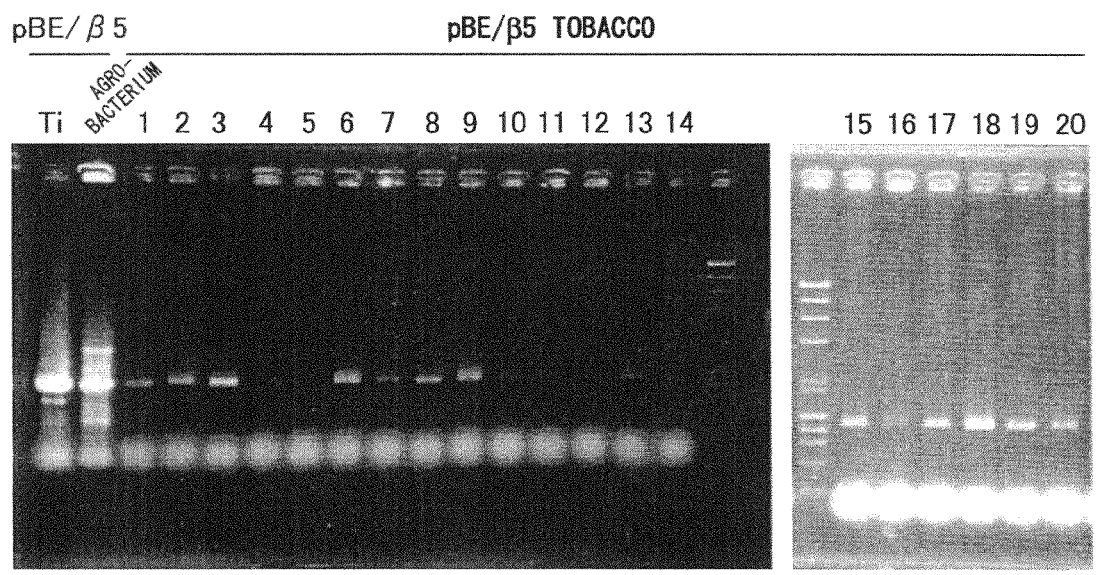
FIG. 2 is a photograph of PCR analysis using the genomic DNA of transformed tobacco as template.

The PCR results are shown in FIG. 2.

EXAMPLE 5

RNA Analysis of the Recombinant Tobacco Introduced With β1,4GT5

RT-PCR was carried out to confirm that human β1,4GT5 was inserted in the tobacco chromosomal genome. For each of the 62 recombinant tobacco strains with confirmed kanamycin resistance, total RNA was extracted (RNeasy Plant Mini Kit, QIAGEN) from about 0.1 g leaf, and PCR was carried out by using a portion of the RNA as template. As primers, b14GT5sqp1 (5'-TGGATTACATTCATGAACTC/ SEQ ID NO: 7) and b14GT5/27R (5'-TCAGTACTCGT-TCACCTGAGCCAGCTC/SEQ ID NO: 4) were used. For RT-PCR, Ready-To-Go RT-PCR Beads (Amersham) were used, and a reverse transcription reaction was carried out at 42° C. for 30 minutes, followed by treatment at 95° C. for five minutes to inactivate the enzymes. Then, a PCR reaction of 95° C., 30 seconds, 55° C., 30 seconds, and 72° C., 2 minutes was repeated 40 times. In five of the 27 clones examined, β1,4GT5-specific bands were found, confirming that the RNA is indeed transcribed.

Figure 3:
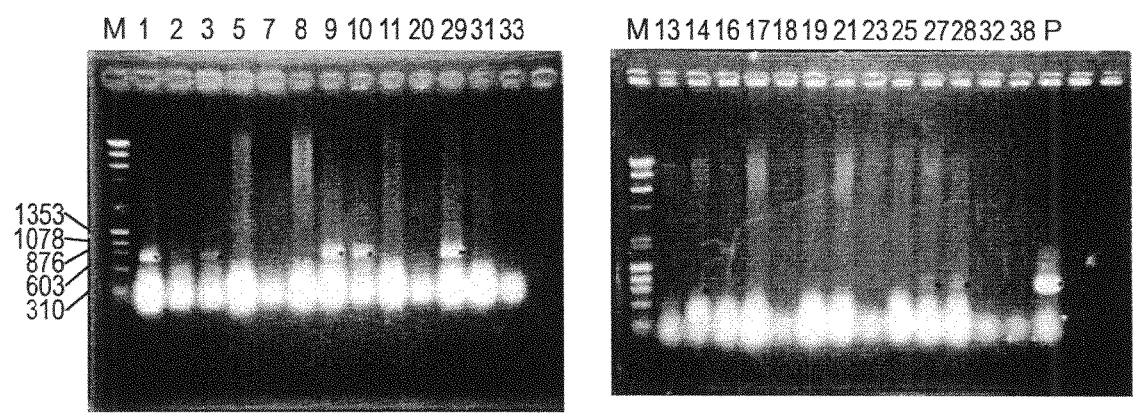
FIG. 3 is a photograph of RT-PCR analysis using the RNA of transformed tobacco as template.

The RT-PCR results are shown in FIG. 3.

EXAMPLE 6

Lipid Analysis of the Recombinant Tobacco

About 10 g of tobacco leaves were cut into the size of about 1 cm square, and after addition of 100 ml chloroform/methanol (1:2), they were homogenized with a Polytron homogenizer for one minute. This was suction filtered through four layers of Miracloth in a Buchner funnel and separated into two layers by adding chloroform and water according to the Bligh-Dyer method, and the chloroform fraction was collected. This fraction was dried under reduced pressure and then dissolved in 1 ml of chloroform/methanol (2:1) to make a total lipid fraction.

The weak-alkaline degradation method was used to obtain sphingolipids from the total lipid fraction. 10 ml of a 0.4 M KOH methanol solution was added to the total lipid obtained above. This was allowed to react at 37° C. for two hours and separated into two layers by adding chloroform and water. Alkaline-resistant lipids were recovered and dried under reduced pressure, and then they were dissolved in a small amount of chloroform/methanol (2:1) to give a total sphingolipid fraction.

EXAMPLE 7

Identification of TLC-Fractionated Lactosylceramide

Sphingolipids were subjected to silica gel TLC to separate them into lipid classes. The total sphingolipid fraction was applied to silica gel TLC, and developed using chloroform/methanol/water (65:16:1) as a developing solvent. The primuline method and the orcinol-sulfuric acid method were used for lipid detection. As a result, spots of newly synthesized lactosylceramide in the lipid of tobacco leaves along with those of glucosylceramide were confirmed.

Figure 4:
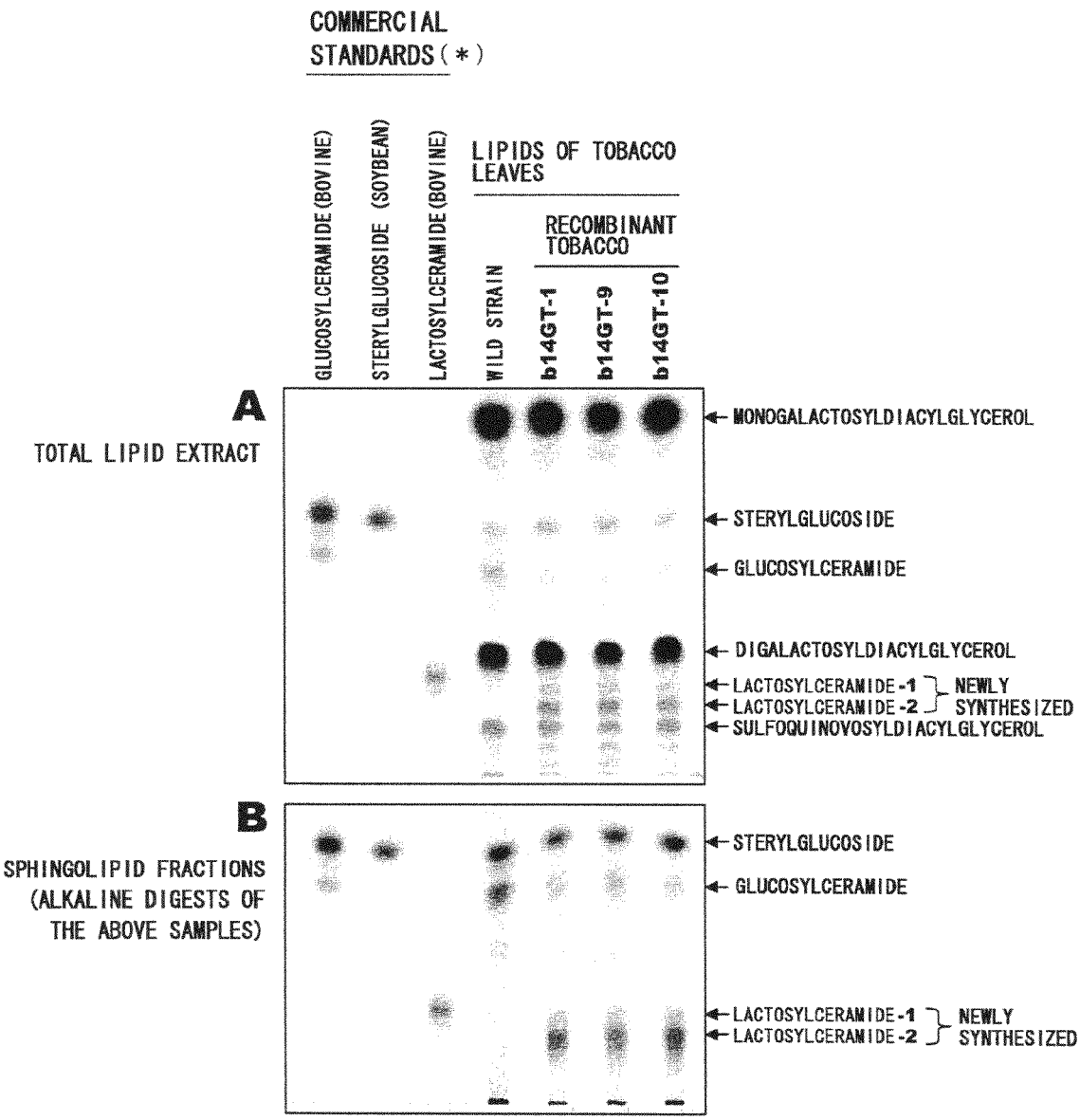
FIG. 4 is a photograph of analysis of the sphingoglycolipids in transformed tobacco. Animal-derived sphingoglycolipids (commercially available standards, * mark) are different in their fatty acid chains (chain length, presence or absence of OH-residue and such) from the lipids synthesized in plants; therefore, their mobilities on TLC differ subtly.

The TLC spots are shown in the photograph of FIG. 4.

EXAMPLE 8

Sugar Chain Analysis of Lactosylceramide

The obtained lactosylceramide was separated and collected from TLC, and analyzed for its sugar chain structure. The sugar chains were cut out with endoglycoceramidase (TAKARA) and developed on TLC. The sugar chain structure was confirmed to be lactose.

Figure 5:
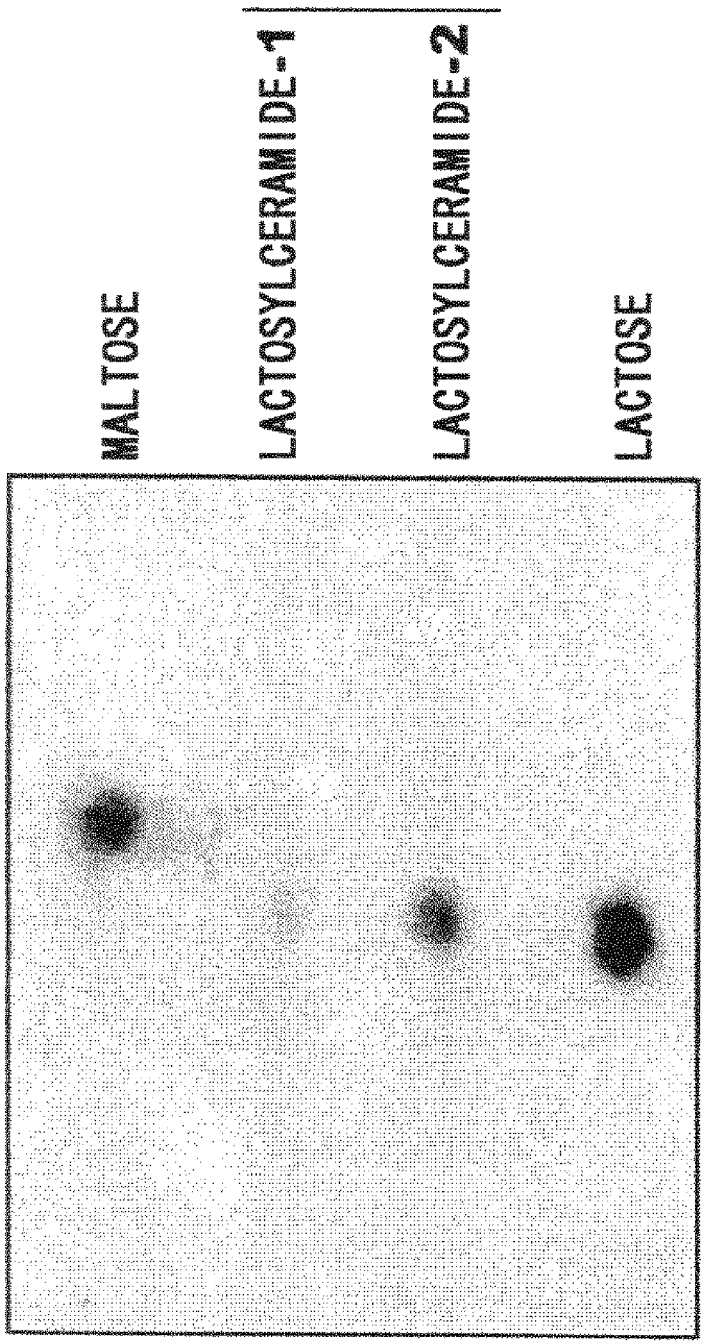
FIG. 5 is a photograph of analysis of the lactosylceramide sugar chains in transformed tobacco.

The TLC photograph is shown in FIG. 5.

EXAMPLE 9

TOF-MASS Analysis of Lactosylceramide

Lactosylceramide-specific peaks (marked with *) were detected through TOF-MASS analysis of the obtained lactosylceramide.

Figure 6:
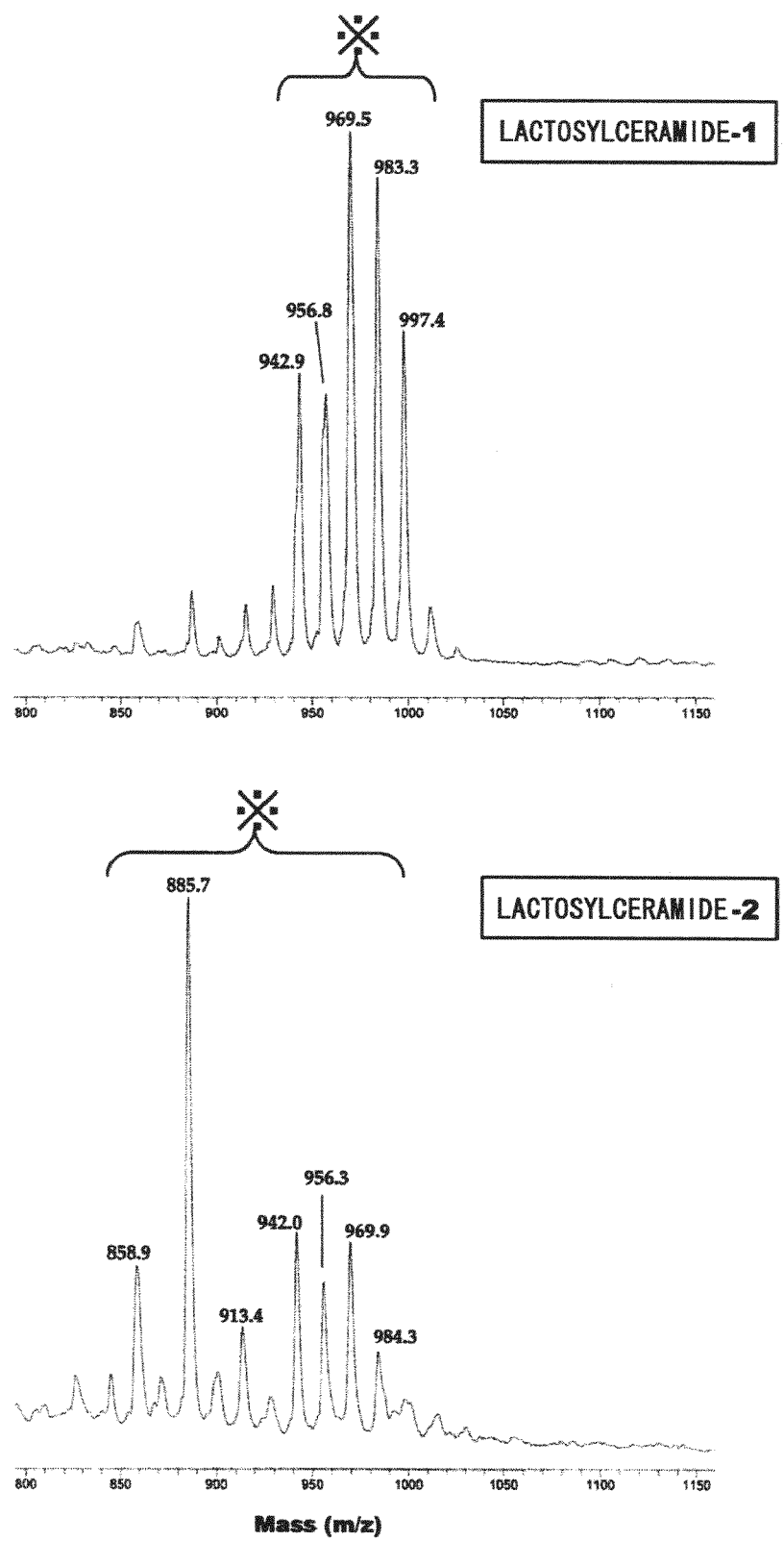
FIG. 6 is a diagram of TOF-MASS analysis of the lactosylceramide in transformed tobacco expressing a human-derived β1,4GT5 gene.
Figure 7:
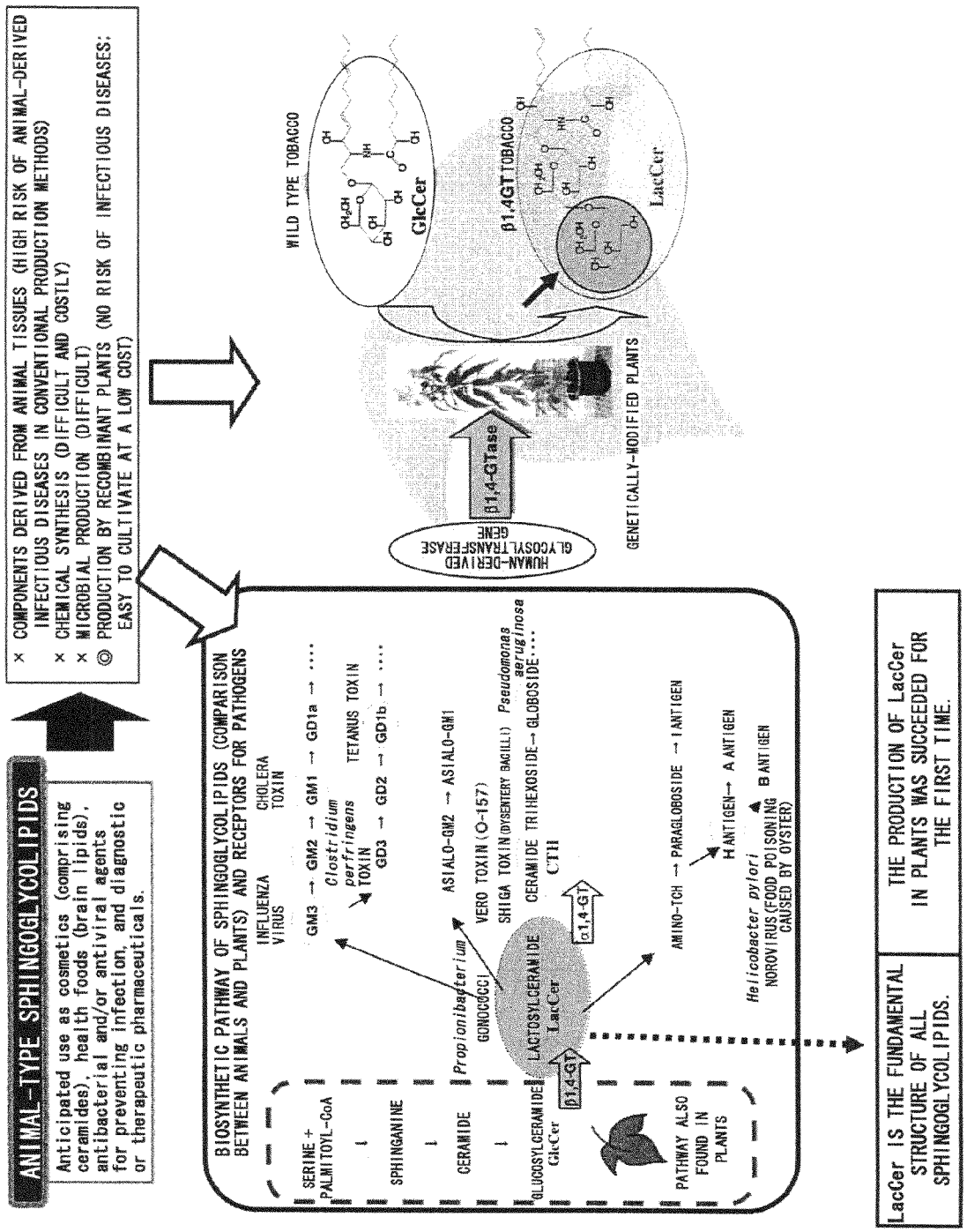
FIG. 7 is a diagram showing problems of the prior art in producing animal-type sphingoglycolipids, pathways for the biosynthesis of sphingoglycolipids (comparison between animals and plants), receptors for pathogenic agents, and transformed tobacco expressing a human-derived β1,4GT5 gene according to the present invention.

The TOF-MASS chromatogram is shown in FIG. 6.

EXAMPLE 10

Lactosylceramide Content Analysis

Colors of the TLC-separated sphingolipids were developed by the orcinol-sulfuric acid method, and the lactosylceramide content was determined by a densitometer method. The coloration with orcinol in the TLC of FIG. 4 was read using a densitometer, and all the lipids were quantified to analyze the relative amount of each lipid and the absolute amount of lactosylceramide. The lipid composition is shown in Table 1 below.

TABLE 1

| | Wild strain | Transformed tobacco | | |
| --- | --- | --- | --- | --- |
| | | b14GT-1 | b14GT-9 | b14GT-10 |
| | | (weight (%)) | | |
| MGDG | 55.0 (±1.0) | 50.7 (±1.0) | 48.8 (±0.7) | 50.7 (±1.2) |
| DGDG | 33.4 (±1.2) | 34.2 (±1.3) | 33.6 (±1.2) | 34.1 (±1.1) |

TABLE 1-continued

| | Wild strain | Transformed tobacco | | |
| --- | --- | --- | --- | --- |
| | | b14GT-1 | b14GT-9 | b14GT-10 |
| | | (weight (%)) | | |
| SQDG | 6.4 (±0.4) | 4.8 (±0.5) | 4.8 (±0.2) | 5.7 (±0.3) |
| SteGlc | 2.1 (±0.3) | 3.3 (±0.2) | 4.0 (±0.3) | 2.6 (±0.2) |
| GlcCer | 3.9 (±0.5) | 0.6 (±0.1) | 0.3 (±0.1) | 0.8 (±0.1) |
| LacCer-1 | 0 (±0) | 1.2 (±0.3) | 2.2 (±0.2) | 1.7 (±0.2) |
| LacCer-2 | 0 (±0) | 5.3 (±0.2) | 6.8 (±0.4) | 5.0 (±0.5) |

Mean value (± standard error);
results of n = 7 experiment;
tr, 0.4% or less;
MGDG, monogalactosyldiacylglycerol;
DGDG, digalactosyldiacylglycerol,;
SQDG, sulfoquinovosyldiacylglycerol;
SteGlc, sterylglucoside;
LacCer, lactosylceramide.

The lactosylceramide content of the transformed tobacco strains (μg/g fresh leaf) is shown in Table 2 below.

TABLE 2

| Wild strain | 0 (±0) |
| --- | --- |
| b14GT-1 | 258 (±49) |
| b14GT-9 | 231 (±33) |
| b14GT-10 | 214 (±41) |

Mean value (± standard error);
results of n = 6 experiments.

As a result, the recombinant tobacco introduced with human β1,4GT5 was found to contain about 200 μg of lactosylceramide in 1 g of fresh leaves (variation among individuals: 157-263 μg).

Previously, the present inventors tried to synthesize lactosylceramide by introducing the β1,4-galactosyltransferase gene (Accession No. AF097159 (NCBI)) into tobacco; however the amount of lactosylceramide obtained then was 0.1 μg per 1 g of fresh leaves, which is not an amount sufficient for industrial application. To the contrary, an amount of lactosylceramide as large as about 2000 times was obtained by the present invention; therefore, it can be said that the present invention is much more useful than conventional methods.

INDUSTRIAL APPLICABILITY

The present invention made it possible to mass synthesize lactosylceramide by using recombinant plants. Lactosylceramide is a precursor common to animal-specific sphingoglycolipids, which are not usually produced in plants. Although sphingoglycolipids are industrially useful, their production has been difficult due to the problems of cost and safety. Owing to the production of this lactosylceramide in plants, it is now possible to mass produce animal-specific sphingoglycolipids at a low cost. The methods of the present invention also have a safety advantage because they use plants in the production process.

The invention claimed is:

1. A transformed plant cell which produces lactosylceramide, wherein the plant cell comprises a promoter expressible in plant cells operably linked to a DNA encoding a human β,4-galactosyltransferase GT5; wherein the DNA is inserted into the chromosomal genome of the plant cell, and the DNA is any one of:
   (a) a DNA encoding a protein comprising the amino acid sequence of SEQ ID NO: 2, or
   (b) a DNA comprising the nucleotide sequence of SEQ ID NO: 1.

2. A transgenic plant which produces lactosylceramide, wherein the plant comprises the transformed plant cell of claim 1.

3. A transgenic plant which produces lactosylceramide, wherein the plant is a progeny or clone of the plant of claim 2.

4. A propagation material of a plant that produces lactosylceramide, wherein the propagation material comprises the transformed plant cell of claim 1.

5. A method of producing a plant which produces lactosylceramide, wherein the method comprises:
   (i) introducing a vector into a plant cell, wherein the vector comprises a promoter expressible in plant cells operably linked to a DNA encoding a human β1,4-galactosyltransferase GT5; wherein the vector is inserted into the chromosomal genome of the plant cell, and the DNA is any one of:
      (a) a DNA encoding a protein comprising the amino acid sequence of SEQ ID NO: 2, or
      (b) a DNA comprising the nucleotide sequence of SEQ ID NO: 1; and
   (ii) regenerating a plant from the transformed plant cell introduced with the vector in step (i), thereby producing a plant that produces lactosylceramide.

6. A method of producing lactosylceramide, wherein the method comprises using the transformed plant cell of claim 1, the plant of claim 2 or 3, or the propagation material of claim 5 to produce lactosylceramide; and extracting the lactosylceramide from the transformed plant cell, the plant, or the propagation material.

7. A propagation material of the plant of claim 3, wherein the plant produces lactosylceramide, and the propagation material comprises a promoter expressible in plant cells operably linked to a DNA encoding a human β1,4-galactosyltransferase GT5; wherein the DNA is inserted into the chromosomal genome of a cell of the propagation material, and the DNA is any one of:
   (a) a DNA encoding a protein comprising the amino acid sequence of SEQ ID NO: 2, or
   (b) a DNA comprising the nucleotide sequence of SEQ ID NO: 1.

* * * * *

UNITED STATES PATENT AND TRADEMARK OFFICE
CERTIFICATE OF CORRECTION

| | | |
|---|---|---|
| PATENT NO. | : 7,943,820 B2 | Page 1 of 1 |
| APPLICATION NO. | : 11/574466 | |
| DATED | : May 17, 2011 | |
| INVENTOR(S) | : Yasushi Tasaka, Takeshi Matsumura and Kouki Matsuo | |

It is certified that error appears in the above-identified patent and that said Letters Patent is hereby corrected as shown below:

Please replace column 23, lines 15-16 with the following corrected version:

-- in plant cells operably linked to a DNA encoding a human
$\beta\underline{1}$,4-galactosyltransferase GT5; wherein the DNA is inserted --

Signed and Sealed this
Ninth Day of August, 2011

David J. Kappos
*Director of the United States Patent and Trademark Office*

SEQUENCE LISTING

<160> NUMBER OF SEQ ID NOS: 7

<210> SEQ ID NO 1
<211> LENGTH: 1167
<212> TYPE: DNA
<213> ORGANISM: Homo sapiens

```
<220> FEATURE:
<221> NAME/KEY: CDS
<222> LOCATION: (1)..(1167)
<223> OTHER INFORMATION:

<400> SEQUENCE: 1 atg cgc gcc cgc cgg ggg ctg ctg cgg ctg ccg cgc tcg ctg ctc        48
Met Arg Ala Arg Arg Gly Leu Leu Arg Leu Pro Arg Arg Ser Leu Leu
1               5                   10                  15 gcc gcg ctc ttc ttc ttt tct ctc tcc tcg ctg ctg tac ttc gtc        96
Ala Ala Leu Phe Phe Phe Ser Leu Ser Ser Leu Leu Tyr Phe Val
            20                  25                  30 tat gtg gcg ccc ggc ata gtg aac acc tac ctc ttc atg atg caa gcc   144
Tyr Val Ala Pro Gly Ile Val Asn Thr Tyr Leu Phe Met Met Gln Ala
35                  40                  45 caa ggc att ctg atc cgg gac aac gtg aga aca atc ggt gct cag gtt   192
Gln Gly Ile Leu Ile Arg Asp Asn Val Arg Thr Ile Gly Ala Gln Val
    50                  55                  60 tat gag cag gtg ctt cgg agt gct tat gcc aag agg aac agc agt gta   240
Tyr Glu Gln Val Leu Arg Ser Ala Tyr Ala Lys Arg Asn Ser Ser Val
65                  70                  75                  80 aat gac tca gat tat cct ctt gac ttg aac cac agt gaa acc ttc ctg   288
Asn Asp Ser Asp Tyr Pro Leu Asp Leu Asn His Ser Glu Thr Phe Leu
                85                  90                  95 caa act aca aca ttt ctt cct gaa gac ttc acc tac ttt gca aac cat   336
Gln Thr Thr Thr Phe Leu Pro Glu Asp Phe Thr Tyr Phe Ala Asn His
            100                 105                 110 acc tgc cct gaa aga ctc cct tcc atg aag ggc cca ata gac ata aac   384
Thr Cys Pro Glu Arg Leu Pro Ser Met Lys Gly Pro Ile Asp Ile Asn
        115                 120                 125 atg agt gaa att gga atg gat tac att cat gaa ctc ttc tcc aaa gac   432
Met Ser Glu Ile Gly Met Asp Tyr Ile His Glu Leu Phe Ser Lys Asp
    130                 135                 140 cca acc atc aag ctc gga ggt cac tgg aag cct tct gat tgc atg cct   480
Pro Thr Ile Lys Leu Gly Gly His Trp Lys Pro Ser Asp Cys Met Pro
145                 150                 155                 160 cgg tgg aag gtg gcg atc ctt atc ccc ttc cgg aac cgc cac gag cac   528
Arg Trp Lys Val Ala Ile Leu Ile Pro Phe Arg Asn Arg His Glu His
                165                 170                 175 ctc cca gtc ctg ttc aga cac ctg ctt ccc atg ctc cag cgc cag cgc   576
Leu Pro Val Leu Phe Arg His Leu Leu Pro Met Leu Gln Arg Gln Arg
            180                 185                 190 ttg cag ttt gca ttt tat gtg gtt gaa caa gtt ggt acc caa ccc ttt   624
Leu Gln Phe Ala Phe Tyr Val Val Glu Gln Val Gly Thr Gln Pro Phe
        195                 200                 205 aat cga gcc atg ctt ttc aac gtt ggc ttt caa gaa gca atg aaa gac   672
Asn Arg Ala Met Leu Phe Asn Val Gly Phe Gln Glu Ala Met Lys Asp
    210                 215                 220 ttg gat tgg gac tgt ttg att ttt cat gat gta gat cac ata ccg gaa   720
Leu Asp Trp Asp Cys Leu Ile Phe His Asp Val Asp His Ile Pro Glu
225                 230                 235                 240 agt gat cgc aac tat tat gga tgt gga cag atg ccg agg cat ttt gca   768
Ser Asp Arg Asn Tyr Tyr Gly Cys Gly Gln Met Pro Arg His Phe Ala
                245                 250                 255 acc aaa ttg gat aag tat atg tat ctg ctt cct tat acc gag ttc ttt   816
Thr Lys Leu Asp Lys Tyr Met Tyr Leu Leu Pro Tyr Thr Glu Phe Phe
            260                 265                 270 ggc gga gtg agt ggc tta aca gtg gaa caa ttt cgg aaa atc aat ggc   864
Gly Gly Val Ser Gly Leu Thr Val Glu Gln Phe Arg Lys Ile Asn Gly
        275                 280                 285 ttt cct aat gct ttc tgg ggt tgg ggt gga gaa gat gac gac ctc tgg   912
Phe Pro Asn Ala Phe Trp Gly Trp Gly Gly Glu Asp Asp Asp Leu Trp
```

```
                    Phe Pro Asn Ala Phe Trp Gly Trp Gly Gly Glu Asp Asp Leu Trp
                        290             295                 300 aac aga gta cag aat gca ggc tat tct gtg agc cgg cca gag ggt gac              960
Asn Arg Val Gln Asn Ala Gly Tyr Ser Val Ser Arg Pro Glu Gly Asp
305                 310                 315                 320 aca gga aag tac aag tcc att cct cat cac cat cga gga gaa gtc cag             1008
Thr Gly Lys Tyr Lys Ser Ile Pro His His His Arg Gly Glu Val Gln
                325                 330                 335 ttt ctt gga agg tat gct ctg ctg agg aag tca aaa gaa cgg caa ggg             1056
Phe Leu Gly Arg Tyr Ala Leu Leu Arg Lys Ser Lys Glu Arg Gln Gly
                340                 345                 350 ctg gat ggc ctc aac aac ctg aac tac ttt gca aac atc aca tac gac             1104
Leu Asp Gly Leu Asn Asn Leu Asn Tyr Phe Ala Asn Ile Thr Tyr Asp
                355                 360                 365 gcc ttg tat aaa aac ata act gtc aac ctg aca ccc gag ctg gct cag             1152
Ala Leu Tyr Lys Asn Ile Thr Val Asn Leu Thr Pro Glu Leu Ala Gln
370                 375                 380 gtg aac gag tac tga                                                         1167
Val Asn Glu Tyr
385

<210> SEQ ID NO 2
<211> LENGTH: 388
<212> TYPE: PRT
<213> ORGANISM: Homo sapiens

<400> SEQUENCE: 2

Met Arg Ala Arg Arg Gly Leu Leu Arg Leu Pro Arg Arg Ser Leu Leu
1               5                   10                  15

Ala Ala Leu Phe Phe Phe Ser Leu Ser Ser Leu Leu Tyr Phe Val
            20                  25                  30

Tyr Val Ala Pro Gly Ile Val Asn Thr Tyr Leu Phe Met Met Gln Ala
            35                  40                  45

Gln Gly Ile Leu Ile Arg Asp Asn Val Arg Thr Ile Gly Ala Gln Val
        50                  55                  60

Tyr Glu Gln Val Leu Arg Ser Ala Tyr Ala Lys Arg Asn Ser Ser Val
65                  70                  75                  80

Asn Asp Ser Asp Tyr Pro Leu Asp Leu Asn His Ser Glu Thr Phe Leu
                85                  90                  95

Gln Thr Thr Thr Phe Leu Pro Glu Asp Phe Thr Tyr Phe Ala Asn His
            100                 105                 110

Thr Cys Pro Glu Arg Leu Pro Ser Met Lys Gly Pro Ile Asp Ile Asn
        115                 120                 125

Met Ser Glu Ile Gly Met Asp Tyr Ile His Glu Leu Phe Ser Lys Asp
130                 135                 140

Pro Thr Ile Lys Leu Gly Gly His Trp Lys Pro Ser Asp Cys Met Pro
145                 150                 155                 160

Arg Trp Lys Val Ala Ile Leu Ile Pro Phe Arg Asn Arg His Glu His
                165                 170                 175

Leu Pro Val Leu Phe Arg His Leu Leu Pro Met Leu Gln Arg Gln Arg
            180                 185                 190

Leu Gln Phe Ala Phe Tyr Val Val Glu Gln Val Gly Thr Gln Pro Phe
        195                 200                 205

Asn Arg Ala Met Leu Phe Asn Val Gly Phe Gln Glu Ala Met Lys Asp
210                 215                 220

Leu Asp Trp Asp Cys Leu Ile Phe His Asp Val Asp His Ile Pro Glu
225                 230                 235                 240
```

Ser Asp Arg Asn Tyr Tyr Gly Cys Gly Gln Met Pro Arg His Phe Ala
            245                 250                 255

Thr Lys Leu Asp Lys Tyr Met Tyr Leu Leu Pro Tyr Thr Glu Phe Phe
        260                 265                 270

Gly Gly Val Ser Gly Leu Thr Val Glu Gln Phe Arg Lys Ile Asn Gly
    275                 280                 285

Phe Pro Asn Ala Phe Trp Gly Trp Gly Gly Glu Asp Asp Asp Leu Trp
290                 295                 300

Asn Arg Val Gln Asn Ala Gly Tyr Ser Val Ser Arg Pro Glu Gly Asp
305                 310                 315                 320

Thr Gly Lys Tyr Lys Ser Ile Pro His His Arg Gly Glu Val Gln
                325                 330                 335

Phe Leu Gly Arg Tyr Ala Leu Leu Arg Lys Ser Lys Glu Arg Gln Gly
            340                 345                 350

Leu Asp Gly Leu Asn Asn Leu Asn Tyr Phe Ala Asn Ile Thr Tyr Asp
        355                 360                 365

Ala Leu Tyr Lys Asn Ile Thr Val Asn Leu Thr Pro Glu Leu Ala Gln
    370                 375                 380

Val Asn Glu Tyr
385

<210> SEQ ID NO 3
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 3
atgcgcgccc gccgggggct gctgcgg                                        27

<210> SEQ ID NO 4
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 4
tcagtactcg ttcacctgag ccagctc                                        27

<210> SEQ ID NO 5
<211> LENGTH: 29
<212> TYPE: DNA
<213> ORGANISM: Artificial
<220> FEATURE:
<223> OTHER INFORMATION: An artificially synthesized primer sequence

<400> SEQUENCE: 5
ttgggatcca tgcgcgcccg ccggggggg                                      29

<210> SEQ ID NO 6
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 6
aaggagctct cagtactcgt tcacctgagc                                     30

<210> SEQ ID NO 7

```
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 7
tggattacat tcatgaactc                                              20
```